US010842865B2

(12) United States Patent
Suer et al.

(10) Patent No.: US 10,842,865 B2
(45) Date of Patent: Nov. 24, 2020

(54) MACADAMIA ALLERGEN

(71) Applicant: EUROIMMUN MEDIZINISCHE LABORDIAGNOSTIKA AG, Luebeck (DE)

(72) Inventors: Waltraud Suer, Buchholz (DE); Stefanie Rohwer, Kalkhorst (DE); Yvonne Denno, Luebeck (DE)

(73) Assignee: EUROIMMUN Medizinische Labordiagnostika AG, Luebeck (DE)

( * ) Notice: Subject to any disclaimer, the term of this patent is extended or adjusted under 35 U.S.C. 154(b) by 560 days.

(21) Appl. No.: 15/414,380

(22) Filed: Jan. 24, 2017

(65) Prior Publication Data

US 2017/0209566 A1      Jul. 27, 2017

(30) Foreign Application Priority Data

Jan. 25, 2016 (EP) .................................... 16000165

(51) Int. Cl.
| | |
|---|---|
| *A61K 39/35* | (2006.01) |
| *C07K 14/415* | (2006.01) |
| *C07K 16/16* | (2006.01) |
| *G01N 33/68* | (2006.01) |

(52) U.S. Cl.
CPC ............ *A61K 39/35* (2013.01); *C07K 14/415* (2013.01); *C07K 16/16* (2013.01); *G01N 33/6854* (2013.01); *G01N 2333/415* (2013.01)

(58) Field of Classification Search
None
See application file for complete search history.

(56) References Cited

U.S. PATENT DOCUMENTS

| | | |
|---|---|---|
| 7,381,534 B1 | 6/2008 | Roux et al. |
| 7,537,914 B1 | 5/2009 | Roux et al. |
| 7,538,203 B1 | 5/2009 | Roux et al. |
| 8,114,605 B1 | 2/2012 | Roux et al. |
| 8,409,582 B1 | 4/2013 | Roux et al. |
| 9,296,798 B1 | 3/2016 | Roux et al. |
| 2003/0124060 A1 | 7/2003 | Roux et al. |
| 2009/0092959 A1 | 4/2009 | Roux et al. |
| 2010/0311603 A1 | 12/2010 | Roux et al. |

FOREIGN PATENT DOCUMENTS

WO        2004/042026 A2       5/2004

OTHER PUBLICATIONS

UniProt Accession No. Q9SPL3 (https://www.uniprot.org/uniprot/Q9SPL3) Jul. 20, 2019.*
Lerner et al. 'Tapping the immunological repertoire to produce antibodies of predetermined specificity.' Nature 299(5884):593-596, 1982.*
Marcus et al. 'A family of antimicrobial peptides is produced by processing of a 7S globulin protein in Macadamia integrifolia kernels.' The Plant Journal. 19(6):699-710, 1999.*
Kurien B.T. (2009) Affinity Purification of Autoantibodies from an Antigen Strip Excised from a Nitrocellulose Protein Blot. In: Kurien B., Scofield R. (eds) Protein Blotting and Detection. Methods in Molecular Biology (Methods and Protocols), vol. 536. Humana Press, Totowa, NJ.*
Blumenthal et al. 'Definition of an Allergen.' Allergens and Allergen Immunotherapy. Ed. R Lockey, S. Bukantz and J. Bousquet. New York: Marcel Decker, 2004.37-50.*
U.S. Appl. No. 15/143,011, filed Apr. 29, 2016, US 2016-0320407 A1, Anna Ehlers.
Extended European Search Report dated Jun. 14, 2016 in Patent Application No. 16000165.7.
Database Geneseq [Online] Jun. 15, 2007 (Jun. 15, 2007), "Macadamia Integrifolia Antimicrobial Protein", XP002758435, retrieved from EBI, accession No. GSP:AAW62830 Database accession No. AAW62830.
Kenneth H. Roux et al: "Tree Nut Allergens", International Archives Of Allergy And Immunology., vol. 131, No. 4, 20, XP055277661, Aug. 20, 2003, pp. 234-244.
Barre et al: "Vicilin Allergens of Peanut and Tree Nuts (Walnut, Hazelnut and Cashew Nut) Share Structurally Related IgE-binding Epitopes", Molecular Immunology, vol. 45, No. 5, XP022402155, Oct. 29, 2007, pp. 1231-1240.
Beatriz Cabanillas et al., "Pine Nut Allergy: Clinical Features And Major Allergens Characterization", Molecular Nutrition & Food Research, vol. 56, No. 12, XP055277789, Dec. 19, 2012, pp. 1884-1893.
Ghorbani, M., Morgan et al., "Protein Characterisation and Immunochemical Measurements of Residual Macadamia Nut Proteins in Foodstuffs", Food Agr. Immunol., vol. 21, No. 4, Dec. 2010; pp. 347-360.
Herbst et al., "Specific IgE Reactivity and Identification of Potential Allergens in Macadamia Allergy", J.Eur, Acad.Dermatol. Venereol., 2010; 24(11), pp. 1361-1363.
Sathe et al., "Solubilization and Electrophoretic Characterization of Select Edible Nut Seed Proteins", J. Agric. Food.Chem. 2009; vol. 57, No. 17, pp. 7846-7856.
Codreanu, F., "A Novel Immunoassay Using Recombinant Allergens Simplifies Peanut Allergy Diagnosis", Int. Arch. Allergy Immunol. 2011; 154(3), pp. 216-226.

(Continued)

*Primary Examiner* — Nora M Rooney
(74) *Attorney, Agent, or Firm* — Grüneberg and Myers PLLC (57) ABSTRACT

Provided is a polypeptide comprising a macadamia protein running in a 2D SDS PAGE at pH 6.3 to 8.7 and 53 to 67 kDa or a protein running in a 2D SDS PAGE at pH 6.5 to 7.9 and 20 to 25 kDa or an antigenic variant thereof, and a tag for detection and/or purification, a polypeptide fused with the macadamia protein, or the macadamia protein is modified by glycosylation, phosphorylation, acetylation, decarboxylation, citrullination, or hydroxylation.

9 Claims, 4 Drawing Sheets
Specification includes a Sequence Listing.

(56) References Cited

OTHER PUBLICATIONS

Office Action dated Mar. 20, 2019 in European Application No. 16 000 165.7.
Rohwer et al., "*Identification of a major allergen from macadamia nut,*" Poster, Euroimmun AG, Nov. 9, 2017, 1 pg.
Sutherland et al., "*Macadamia nut anaphylaxis: Demonstration of specific IgE reactivity and partial cross-reactivity with hazelnut,*" J. Clin. Immunol., Oct. 1999; 104:889-890.
Wang et al., "*Ana o 1, a cashew (Anacardium occidental) allergen of the vicilin seed storage protein family,*" J. Allergy Clin. Immunol., vol. 110, No. 1, Jul. 2002, pp. 160-166, Jul. 2002, DOI:10.1067/mai.2002.125208.
Office Action dated Aug. 23, 2019 in Taiwanese Application No. 106101600, 5 pages.

\* cited by examiner

MACADAMIA ALLERGEN

CROSS REFERENCE TO RELATED APPLICATIONS

This application claims priority to EP 16000165.7 application filed 25 Jan. 2016, the content of which is incorporated herein by reference in its entirety.

BACKGROUND OF THE INVENTION

Field of Invention

The present invention relates to a polypeptide comprising a macadamia protein selected from the group comprising a protein running in a 2D SDS PAGE at pH 6.3 to 8.7 and 53 to 67 kDa and a protein running in a 2D SDS PAGE at pH 6.5 to 7.9 and 20 to 25 kDa or an antigenic variant thereof, preferably the protein running at pH 6.3 to 8.7 and 53 to 67 kDa or an antigenic variant thereof.

Discussion of the Background

Allergic reactions to tree nuts can be serious and life-threatening. This holds true for common species such as hazelnut, peanut, walnut, but also for the macadamia nut, the fruit of an Australian evergreen tree (*Macadamia tetraphylla* and *M. integrifolia*).

Macadamia nut, which is, in terms of botany, a seed, is not as common as a food as many other tree nuts, but is more and more frequently consumed fresh or roasted and is often added to a variety of foods such as snack bars, cereals and mixed nuts. Ground macadamia meal is becoming an increasingly popular ingredient in baked goods, as is cold pressed macadamia oil. Not in the least, macadamia nut is often available as part of nut mixes and as such sold in countries which did not previously import it.

Allergic reactions caused by exposure to macadamia nuts in sensitized individuals may include serious symptoms (Pallares, D.E. (2000): Allergy to macadamia nut. Ann Allergy Asthma Immunol 2000; 85(5): 385-6). Therefore, it is crucial that subjects suffering from an allergy are aware of the source of allergens, since they need to avoid contact with foodstuffs, cosmetics and other products that contain or have been in contact with any of them.

Allergies may be diagnosed using conventional skin prick assays that involve exposure of the skin of a subject suspected of suffering from an allergy to the extract of a potentially allergenic fruit, complemented with suitable controls. However, false negative results occur frequently, since certain allergens may be present in such extracts at insufficiently low concentrations (Sicherer, S. H., Teuber, S. S. (2004): Current approach to the diagnosis and management of adverse reactions to foods. Journal of Allergy and Clinical Immunology 2004; 114.5, 1146-50). In addition, specific allergens may be subject to proteolysis in extracts (Rancé, F., Juchet, A., Brémont, F., Dutau, G. (1997): Correlation between skin prick tests using commercial extracts and fresh foods, specific IgE and food challenges. Allergy 1997; 52.10, 1031-5). Furthermore, assays based on whole extracts are insufficiently specific owing to cross reactivities.

Therefore, it is desirable to devise assays based on the detection of antibodies such as IgE or IgG to specific allergens. Such assays involve the exposure of a patient sample comprising antibodies to an immobilized allergen followed by detection, optionally quantification of IgE antibodies binding to the immobilized allergen (Volcheck, G. W. (2009): Clinical Allergy, Diagnosis and Management).

Major allergens have been identified in a range of nuts. For example, the vast majority of cases of peanut allergy is associated with sensitivity to storage proteins Ara h 2, Ara h 7 and Ara h 6. Consequently, reasonably reliable assays based on the detection of IgE antibodies to these allergens have been devised (Codreanu, F., Collignon, O., Roitel, O., Thouvenot, B., Sauvage, C., Vilain, A. C., Cousin, M. O., Decoster, A., Renaudin, J. M., Astier, C Monnez, J. M., Vallois, P., Morisset, M., Moneret-Vautrin, D. A., Brulliard, M., Ogier, V., Castelain, M. C., Kanny, G., Bihain, B. E., Jacquenet, S. (2011): A novel immunoassay using recombinant allergens simplifies peanut allergy diagnosis. Int Arch Allergy Immunol 2011; 154(3):216-26; EP15075033.9).

By contrast, very little information is available regarding the identities of macadamia nut allergens. Known described immunoassays for the diagnosis of macadamia allergy so far had to rely on whole nut extracts or partially purified extracts. For example, Ghorbani et al. performed an immunoassay based on the detection of residual macadamia nut proteins in foodstuffs (Ghorbani, M., Morgan, M. R. A. (2010): Protein characterisation and immunochemical measurements of residual macadamia nut proteins in foodstuffs. Food Agr Immunol 2010; 21:347-360).

Herbst et al. used a whole nut extract from a single batch of macadamia nuts which caused a patient to show allergic symptoms (Herbst, R. A., Wahl, R., Frosch, P. J. (2010): Specific IgE reactivity and identification of potential allergens in macadamia allergy. J Eur Acad Dermatol Venereol 2010; 24(11):1361-3).

Sathe et al. reported the solubilisation and use in a Western blot of full extracts made from various tree nuts including macadamia nut (Sathe, S. K., Venkatachalam, M., Sharma, G. M., Kshirsagar, H. H., Teuber, S. S., Roux, K. H. (2009): Solubilization and electrophoretic characterization of select edible nut seed proteins. J Agric Food Chem 2009; 57(17):7846-56).

In the absence of specific allergens, it is not feasible to provide a sufficiently reliable diagnosis. Whole nut extracts or partially purified extracts are associated with limitations similar to the shortcomings of skin prick assays such as instability and insufficient specificity, more specifically false negative results. Therefore, there still exists a need for better and more effective diagnosis, testing, and treatments of allergic reactions to nuts.

SUMMARY OF THE INVENTION

Accordingly, one object of the present invention is to provide a method for the diagnosis of an allergy, preferably a nut allergy, more preferably a macadamia allergy, and reagents for such a method, which method has an improved diagnostic reliability, in particular sensitivity, when compared to state of the art assays.

A further object of the present invention is to provide an assay for the differential diagnosis of allergies, preferably nut allergies such as tree nut allergies, more preferably for distinguishing an allergy to a macadamia nut from an allergy to a nut other than macadamia, and/or for monitoring the therapy of an individual suffering from such an allergy.

Another object of the present invention is to provide reagents useful for such an assay, methods for making such reagents and methods for such diagnosis.

A further object of the present invention is to provide an isolated or recombinant polypeptide comprising:

a macadamia protein selected from the group consisting of a protein running in a 2D SDS PAGE at pH 6.3 to 8.7 and 53 to 67 kDa and a protein running in a 2D SDS PAGE at pH 6.5 to 7.9 and 20 to 25 kDa and a variant thereof having at least 90% identity, and a tag for detection and/or purification, a polypeptide fused with the macadamia protein, or the macadamia protein is modified by glycosylation, phosphorylation, acetylation, decarboxylation, citrullination, or hydroxylation.

The isolated or recombinant polypeptide may comprise a FLAG GST, His, or MBP tag and/or could be immobilized on a solid support.

Another object of the present invention is to provide a nucleic acid encoding the polypeptide, a vector comprising the nucleic acid, and a host cell comprising the vector.

In one embodiment, the macadamia protein comprises the amino acid sequence of SEQ ID NO:1 or variants thereof. In another embodiment, the polypeptide comprises a fusion polypeptide having the amino acid sequence of SEQ ID NO:2 or variants thereof.

A further object of the present invention is to provide a medical device comprising the polypeptide and a diagnostically useful carrier selected from the group consisting of a bead, a test strip, a microtiter plate, a blot, a glass surface, a slide, a biochip, a membrane, a microarray, an electrophoresis gel, and a microtiter plate. The medical device may comprise a blot selected from the group consisting of a western blot, line blot, and dot blot.

Another object of the present inventions is to provide a method of detecting an antibody to a macadamia protein, the method comprising:

contacting a sample obtained from a subject with a macadamia protein selected from the group comprising a protein running in a 2D SDS PAGE at pH 6.3 to 8.7 and 53 to 67 kDa and a protein running in a 2D SDS PAGE at pH 6.5 to 7.9 and 20 to 25 kDa or a variant thereof, detecting in the sample whether an antibody to the macadamia protein presents in the sample by detecting binding between the antibody and the macadamia protein, and optionally, isolating a complex between the antibody and the protein by removing the sample.

The macadamia protein may be immobilized on a solid support, and the method further optionally may comprise washing the immobilized protein in a washing buffer.

Another object of the present invention is to provide a method for treatment of a nut allergy comprising administrating to a subject in need thereof or contacting with a sample from the subject an effective amount of a macadamia protein selected from the group consisting of a protein running in a 2D SDS PAGE at pH 6.3 to 8.7 and 53 to 67 kDa and a protein running in a 2D SDS PAGE at pH 6.5 to 7.9 and 20 to 25 kDa or a variant thereof. The nut allergy may be a macadamia nut allergy.

A further object of the present invention is to provide an antibody binding to a macadamia protein selected from the group consisting of a protein running in a 2D SDS PAGE at pH 6.3 to 8.7 and 53 to 67 kDa and a protein running in a 2D SDS PAGE at pH 6.5 to 7.9 and 20 to 25 kDa thereof, wherein optionally the antibody is in a complex with the macadamia protein or a variant thereof. In a preferred embodiment, the antibody binding to a macadamia protein is an isolated antibody.

A test kit for diagnosis of a disease is also provided, comprising the polypeptide and a detection device for detection a complex comprising the polypeptide and an antibody that is bound to the polypeptide.

Another object of the present invention is to provide a method for isolating an antibody binding to a macadamia protein selected from the group consisting of a protein running in a 2D SDS PAGE at pH 6.3 to 8.7 and 53 to 67 kDa and a protein running in a 2D SDS PAGE at pH 6.5 to 7.9 and 20 to 25 kDa or an antigenic fragment thereof, the method comprising:

a) contacting a sample comprising an antibody with the macadamia protein or a variant thereof under conditions compatible with formation of a complex, b) isolating the complex formed in a)

c) dissociating the complex isolated in b), and d) separating the antibody from the macadamia protein.

A pharmaceutical composition and a vaccine are also provided, comprising the polypeptide and a pharmaceutically acceptable carrier or an adjuvant.

In one embodiment, the sample is a bodily fluid selected from the group consisting of whole-blood, serum, cerebrospinal fluid, and saliva.

In another embodiment, the antibody is an IgE antibody.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

All methods and materials similar or equivalent to those described herein can be used in the practice or testing of the present invention, with suitable methods and materials being described herein. All publications, patent applications, patents, and other references mentioned herein are incorporated by reference in their entirety. Further, the materials, methods, and examples are illustrative only and are not intended to be limiting, unless otherwise specified.

Generally, objects of the present invention, which will become more apparent in conjunction with the following detailed description of the preferred embodiments, either alone or in combinations thereof, have been satisfied by the inventors' discovery of a polypeptide comprising a macadamia protein selected from the group consisting of a protein running in a 2D SDS PAGE at pH 6.3 to 8.7 and 53 to 67 kDa and a protein running in a 2D SDS PAGE at pH 6.5 to 7.9 and 20 to 25 kDa and a variant thereof, preferably the protein running at pH 6.3 to 8.7 and 53 to 67 kDa or a variant thereof. The polypeptide is preferably a polypeptide from *Macadamia tetraphylla* or *M. integrifolia*, preferably *M. integrifolia*.

In one embodiment, the polypeptide is an isolated and/or recombinant polypeptide. In another embodiment, the polypeptide is a fusion polypeptide, preferably comprising a tag for detection or purification. In yet another embodiment, the polypeptide is immobilized.

Another object of the present invention is to provide a nucleic acid encoding the polypeptide according to one object of the present invention, preferably in a vector, more preferably in a vector in a cell.

Another object of the present invention is to provide a medical device comprising the polypeptide, wherein the medical device is preferably a diagnostically useful carrier, more preferably selected from the group comprising of a bead, a test strip, a microtiter plate, a blot, preferably from the group comprising western blot, line blot and dot blot, a glass surface, a slide, a biochip, a membrane, a microarray, an electrophoresis gel, and a microtiter plate.

A further object of the present invention is to provide a method comprising detecting in a sample, preferably from a mammal, more preferably a human, an antibody binding to the polypeptide, wherein the method is preferably for the diagnosis of a nut allergy, more preferably for the diagnosis of a macadamia allergy.

A further object of the present invention is to provide a method for the treatment of a disease comprising administrating to a subject or contacting with a sample from a subject an effective amount of the polypeptide, wherein the disease is preferably a nut allergy, more preferably a tree nut allergy, most preferably a macadamia allergy, thereby treating the nut allergy.

Another object of the present invention is to provide an antibody binding to a macadamia protein selected from the group consisting of a protein running in a 2D SDS PAGE at pH 6.3 to 8.7 and 53 to 67 kDa and a protein running in a 2D SDS PAGE at pH 6.5 to 7.9 and 20 to 25 kDa, preferably the protein running at pH 6.3 to 8.7 and 53 to 67 kDa, wherein optionally the antibody is in complex with the macadamia protein or a variant thereof.

A further object of the present invention is to provide a test kit for diagnosis of a disease, comprising the polypeptide and optionally a detecting device for detection of a complex comprising the polypeptide and the antibody.

Another object of the present inventions is to provide a method for isolating an antibody binding to a macadamia protein selected from the group consisting of a protein running in a 2D SDS PAGE at pH 6.3 to 8.7 and 53 to 67 kDa and a protein running in a 2D SDS PAGE at pH 6.5 to 7.9 and 20 to 25 kDa or an antigenic fragment thereof, comprising:
  a) contacting a sample comprising the antibody with the macadamia protein or a variant thereof under conditions compatible with the formation of a complex,
  b) isolating the complex formed in a),
  c) dissociating the complex isolated in b), and
  d) separating the antibody from the macadamia protein.

Another object of the present inventions is to provide a pharmaceutical composition or vaccine comprising the polypeptide, optionally comprising, in addition, a pharmaceutically acceptable carrier or an adjuvant.

In one embodiment, the sample is a bodily fluid comprising antibodies, preferably selected from the group consisting of whole-blood, serum, cerebrospinal fluid and saliva, more preferably whole blood.

In another embodiment, the antibody is an IgE or IgG such as IgG4, preferably an IgE antibody.

In one embodiment, the polypeptide is used for diagnosis of an allergy, preferably a nut allergy, more preferably a tree nut allergy, most preferably for a macadamia allergy.

These and other objects of the present invention are based on the inventors' surprising finding that a range of specific allergens exist in macadamia nuts that display reactivity towards the sera from patients suffering from nut allergy and may be used to diagnose and treat a nut allergy, in particular a macadamia allergy. Moreover, these allergens may be used to differentiate nut allergies, in particular to distinguish an allergy to macadamia to an allergy to a nut other than macadamia. As far as the inventors are aware, these antigens have not yet been described as such in the state of the art.

In one embodiment, the term "tree nut", as used herein, is a nut selected from the group consisting of macadamia nut, hazel nut, peanut, walnut, almond, pecan nut, cashew nut, brazil nut, chestnut, pine nut, pistachiao, Mongongo Yeheb nut, Candlenut, and Chilean hazelnut.

In one embodiment, a diagnostically useful carrier is used, which is preferably a solid carrier for contacting a means for specifically capturing an antibody, which means is associated with said carrier, with a bodily fluid sample from a subject, preferably a mammalian subject, more preferably a human subject. The carrier may directly be contacted with a sample and allows exposure of the means for specifically capturing the antibody to any antibodies in the sample. In a preferred embodiment, the solid carrier is a diagnostic device, more preferably selected from the group consisting of a bead, a test strip, a microtiter plate, and a blot, preferably from the group consisting of a western blot, line blot and dot blot, a glass surface, a slide, a biochip, a membrane, a microarray, an electrophoresis gel, and a microtiter plate.

In one embodiment, the diagnostically useful carrier is a line blot (Raoult, D., and Dasch, G. A. (1989), The line blot: an immunoassay for monoclonal and other antibodies. Its application to the serotyping of gram-negative bacteria. J. Tmmunol. Methods, 125 (1-2), 57-65; WO2013041540). The term "line blot", as used herein, refers to a test strip, more preferably membrane-based, that has been coated with one or more means for capturing an antibody, preferably a polypeptide each. If two or more means are used, they are preferably spatially separated on the carrier. Preferably, the width of the bands is at least 30, more preferably 40, 50, 60, 70 or 80% of the width of the test strip. The test strip may comprise one or more control bands for confirming that it has been contacted with a sample sufficiently long and under adequate conditions, in particular in the presence of human serum, an antibody conjugate, or both. A multitude of line blots are commercially available, for example from EUROIMMUN AG, Lubeck, Germany.

Samples used to practice objects of the present invention comprise antibodies, also referred to as immunoglobulins. Typically a sample is a bodily fluid comprising a representative set of the entirety of the subject's immunoglobulins. However, the sample, once provided, may be subjected to further processing which may include fractionation, centrifugation, enriching or isolating the entirety of immunoglobulins or any immunoglobulin class of the subject, preferably IgE and/or IgG4, which may affect the relative distribution of immunoglobulins of the various classes. The sample may be selected from the group consisting of whole-blood, serum, cerebrospinal fluid and saliva and is preferably serum. In one embodiment, the sample comprises IgE class antibodies.

The diagnostically useful carrier comprises a means for specifically capturing an antibody to a macadamia protein running in a 2D SDS PAGE at pH 6.3 to 8.7 and 53 to 67 kDa or a macadamia protein running in a 2D SDS PAGE at pH 6.5 to 7.9 and 20 to 25 kDa, preferably the macadamia protein running at pH 6.3 to 8.7 and 53 to 67 kDa, which has been identified by the inventors as a macadamia vicilin-like protein (database accession code of the polypeptide is Q9SPL3; database accession code of the nucleic acid encoding the protein is AF161885). Any database codes referred to throughout this application refer to the polypeptide sequence available via the NCBT databases as online at the priority date of this application.

In one embodiment, such means for specifically capturing such an antibody is a polypeptide comprising a macadamia protein selected from the group consisting of a protein running in a 2D SDS PAGE at pH 6.3 to 8.7 and 53 to 67 kDa or a protein running in a 2D SDS PAGE at pH 6.5 to 7.9 and 20 to 25 kDa or an variant thereof, preferably the protein running at pH 6.3 to 8.7 and 53 to 67 kDa or a variant thereof.

In one embodiment, the carrier comprises one or more means for specifically capturing an antibody, preferably one or more, more preferably two or more, more preferably three or more, more preferably four or more such means, each of them capable of specifically capturing a different antibody. In addition to a means for capturing an macadamia protein, preferably macadamia Vicilin-like protein (Q9SLP3), the carrier may comprise a means for capturing an antibody to one or more than one protein from the group comprising SEQ ID NO:3 (Cor al1 from hazelnut), SEQ ID NO:4 (Ses i3 from Sesam), SEQ ID NO:5 (Ara h1 from peanut), SEQ ID NO:6 (Pis v3 from pistachio), SEQ ID NO:7 (Ana o1 from cashew), SEQ ID NO:8 (Car i2 from pecan), SEQ ID NO:9 (Jug r2 from walnut), for example a means for capturing an antibody to SEQ ID NO:3 and a means for capturing an antibody to SED ID NO:4. The means is preferably immobilized on a carrier. In another embodiment, a means for specifically capturing an antibody is the polypeptide to which the antibody to be captured binds such as the polypeptide according to the present invention or SEQ ID NO:3 (Cor al1 from hazelnut), SEQ ID NO:4 (Ses i3 from Sesam), SEQ ID NO:5 (Ara h1 from peanut), SEQ ID NO:6 (Pis v3 from pistachio), SEQ ID NO:7 (Ana o1 from cashew), SEQ ID NO:8 (Car i2 from pecan), SEQ ID NO:9 (Jug r2 from walnut), for example a means for capturing an antibody to SEQ ID NO:3 and a means for capturing an antibody to SED ID NO:4 or a variant thereof. The means, together with the insoluble carrier to which it is attached, may be separated from a reaction mixture in a straightforward manner, for example by filtration, centrifugation or decanting. The means may be immobilized in a reversible or irreversible manner. For example, immobilization is reversible if a molecule interacts with the carrier via ionic interactions which may be masked by addition of a high concentration of salt or if the molecule is bound via a cleavable covalent bond. By contrast, immobilization is irreversible if a molecule is tethered to the carrier via a covalent bond that cannot be cleaved in an aqueous solution. The means, preferably the polypeptide, may be indirectly immobilized, for example by immobilizing an antibody or other entity having affinity to the polypeptide, followed by addition of the polypeptide and formation of a polypeptide-antibody complex.

However, the objects of the present invention may not only be carried out using polypeptides having the exact sequences referred to in this application explicitly, for example by function, name, sequence or accession number, or implicitly, or wild type sequences, but also using variants of such polypeptides.

In a preferred embodiment, the term "variant", as used herein, may refer to at least one fragment of a full length sequence referred to, more specifically an amino acid or nucleic acid sequence which is, relative to the full-length sequence, truncated at one or both termini by one or more amino acids. Such a fragment comprises or encodes for a peptide having at least 10, 15, 25, 50, 75, 100, 150, 200, 300, 400 or 500 successive amino acids of the original sequence or a variant thereof. The total length of the variant may be at 25, 30, 40, 50, 60, 70, 80, 90, 100 or more amino acids. In one embodiment, a fragment is SEQ ID NO:1 or a variant thereof.

The variant may be at least 40, 50, 60, 70, 75, 80, 85, 90, 92, 94, 95, 96, 97, 98 or 99% identical to the reference amino acid sequence referred to or the fragment thereof, wherein amino acids other than those essential for the biological activity are deleted or substituted and/or one or more such essential amino acids are replaced in a conservative manner and/or amino acids are added or deleted such that the biological activity of the polypeptide is at least partially preserved. Various methods are know that may be used to align two given nucleic acid or amino acid sequences and to calculate the degree of identity (see for example Arthur Lesk (2008), Introduction to bioinformatics, Oxford University Press, 2008, 3$^{rd}$ edition). In a one embodiment, the ClustalW software (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007): Clustal W and Clustal X version 2.0. Bioinformatics, 23, 2947-2948) is used applying default settings.

In one embodiment, variants may, in addition, comprise chemical modifications, for example, isotopic labels or covalent modifications such as glycosylation, phosphorylation, acetylation, decarboxylation, citrullination, or hydroxylation. The person skilled in the art is familiar with methods for the modification of polypeptides. Moreover, variants may also be generated by way of fusion with other known polypeptides or variants thereof.

The variants of the polypeptide have biological activity. In one embodiment, such biological activity is the ability to bind to an allergy-specific IgE antibody from a patient, preferably a patient suffering from an allergy, more preferably an allergy to a nut, most preferably an allergy to a macadamia. In another embodiment, such biological activity is the ability to elicit an allergic response in a subject allergic to a nut, preferably a tree nut, more preferably a macadamia nut.

The person skilled in the art is capable of designing variants by starting from the original macadamia protein, introducing modifications point mutations, truncations and the like and subsequently confirming that the variant still has biological activity by testing whether said variant binds to an antibody in a sample obtained from a subject allergic to a macadamia nut. Variants may be made using genetic engineering approaches or chemical synthesis.

A binding activity may be determined by a Western blot, using as a source of an antibody serum from a patient allergic to macadamia, preferably as described in the examples.

The polypeptide according to the present invention or a variant thereof may be a fusion protein, i.e. a polypeptide fused, preferably N-terminally or C-terminally, to another sequence, optionally via a linker. The other sequence may be a tag for the detection, for example a FLAG tag, or a tag for purification, for example selected from the group consisting of a GST, His, and MBP tag. An exemplary fusion polypeptide according to the objects of the present invention is shown in SEQ ID NO:2.

The polypeptide according to the object of the present invention may be provided in any form and at any degree of purification, from tissues, fruits or cells comprising said polypeptide in an endogenous form, more preferably cells overexpressing the polypeptide, crude or enriched lysates of such cells, to purified and/or isolated polypeptide which is essentially pure. In a preferred embodiment, the polypeptide is a native polypeptide, wherein the term "native polypeptide", as used herein, refers to a folded polypeptide, more preferably to a folded polypeptide purified from tissues or cells, more preferably from mammalian cells or tissues, optionally from non-recombinant tissues or cell. If a native polypeptide is used, it is preferably enriched compared to its natural state.

In one embodiment, the polypeptide may be a recombinant protein, wherein the term "recombinant", as used herein, refers to a polypeptide produced using genetic engineering approaches at any stage of a production process, for example by fusing a nucleic acid encoding the polypeptide to a strong promoter for overexpression in cells or tissues or by engineering the sequence of the polypeptide itself and/or using for expression in a cell modified by genetic engineering. The person skilled in the art is familiar with methods for engineering nucleic acids and encoded polypeptides (for example, described in Sambrook, J., Fritsch, E. F. and Maniatis, T. (1989), Molecular Cloning, CSH or in Brown T. A. (1986), Gene Cloning—an introduction, Chapman & Hall) and for producing and purifying native or recombinant polypeptides (for example Handbooks "Strategies for Protein Purification", "Antibody Purification", published by GE Healthcare Life Sciences, and in Burgess, R. R., Deutscher, M. P. (2009): Guide to Protein Purification).

In one embodiment, the term "isolated" means that the polypeptide has been enriched relative to the entirety of the macadamia proteins, preferably macadamia allergens, in a whole nut or whole nut extract obtained from a whole nut. In another embodiment, the polypeptide is an isolated polypeptide, wherein the term "isolated" means that the polypeptide has been enriched compared to its state upon production using a biotechnological or synthetic approach and is preferably pure, i.e. at least 10, 20, 30, 40, 50, 60, 70, 80, 90, 95 or 99% of the polypeptide used consists of said polypeptide as judged by SDS polyacrylamide gel electrophoresis followed by Coomassie blue staining and visual inspection.

In one embodiment, the subject is an animal including a human producing antibodies, preferably IgE class or equivalent allergy-related antibodies, more preferably from a mammal, most preferably a human.

A method according to one object of the present invention contemplates detecting in a sample an antibody binding to the polypeptide, which method is preferably for the diagnosis of a nut allergy, more preferably for the diagnosis of a macadamia allergy. Various known methods may be used to detect an antibody in a sample, for example selected from the group consisting of an immunodiffusion technique, basophil activation by IgE antibody, immunoelectrophoretic technique, light scattering immunoassay, agglutination technique, labeled immunoassay such as a radiolabeled immunoassay, enzyme immunoassays such as a colourimetric assay, a chemiluminscence immunoassay and a immunofluorescence technique.

In some embodiments, detecting the absence or presence of an antibody, optionally meaning determining whether the concentration of the antibody is beyond a certain threshold, often suggested by the detection limit, in the sample, is sufficient for the diagnosis. If the antibody can be detected, this will be information instrumental for the clinician's diagnosis and indicates the increased likelihood that a patient suffers from an allergy. In one embodiment, the relative concentration of the antibody in serum, compared to the level that may be found in the average healthy subject, may be determined. In one embodiment, the term "detecting the presence or absence", as used herein, means that it is sufficient to check whether a signal sufficiently beyond any background level may be detected using a suitable complex detection method that indicates that the antibody of interest is present or more antibody of interest is present than would be in a healthy subject. In one embodiment, this may involve determining whether the concentration is beyond the concentration in a control or beyond a threshold, preferably at least 0.1, preferably 0.2, 0.5, 1, 2, 5, 10, 20, 25, 50, 100, 200, 500, 1000, 10000 or 100000 times higher than the concentration of the antibody of interest found in an average healthy subject.

Briefly, detecting the antibody may involve a) contacting a sample comprising the antibody with the polypeptide according to the present invention or a variant thereof under conditions compatible with formation of a complex. This may be achieved by contacting a liquid sample with the polypeptide in an immobilized form, for example immobilized on a membrane such as used in a Western blot or a line blot. As the sample and the polypeptide are in contact, any antibody present in the sample which is capable of binding specifically to the polypeptide will do so to the effect that a complex comprising the polypeptide and the antibody is present.

Subsequently, b) is carried out which involves isolating said complex formed in a), for example by removing the sample and, optionally, washing the immobilized polypeptide using a washing buffer.

Then c) involves detecting the complex, for example by adding a secondary antibody which may bind to the antibody from the sample. The secondary antibody may comprise a label, for example an enzyme or a radioactive isotope. Alternatively, the complex may be detected directly using methods such as chemical crosslinking followed by SDS PAGE or using mass spectrometry.

The detection of an antibody to the polypeptide according to the present invention suggests that the subject donating a sample is allergic to macadamia. In case a subject shows allergic responses, but such a sample does not contain antibodies to the inventive subject, it is likely that the subject suffers from an allergy, for example a nut allergy, but is not allergic to macadamia nut.

In one embodiment, a diagnostically useful carrier comprises a means for specifically capturing an antibody to the polypeptide. In one embodiment, the term "specifically capturing an antibody", as used herein, refers to the ability to bind specifically to the antibody of interest to the effect that it is bound and removed from the sample, whereas other antibodies are essentially not bound and remain in the sample.

According to one object of the present invention, a means for specifically detecting a captured antibody is provided, optionally as part of a kit. In one embodiment, the term "specifically detecting a captured antibody", as used herein, means that the antibody binding specifically to the means for specifically capturing the antibody binding to the polypeptide according to the invention, following capture, is detected rather than any other antibody present in the sample. In one embodiment, the term "binding specifically", as used herein, means that the binding is stronger than a binding reaction characterized by a dissociation constant of $1\times10^{-5}$M, more preferably $1\times10^{-7}$M, more preferably $1\times10^{-8}$M, more preferably $1\times10^{-9}$ M, more preferably $1\times10^{-10}$ M, more preferably $1\times10^{-11}$M, more preferably $1\times10^{-12}$M, as determined by surface plasmon resonance using Biacore equipment at 25° C. in PBS buffer at pH 7.

Also provided is a kit, preferably for diagnosing an allergy, more preferably for diagnosing a macadamia allergy. Such a kit is a container that comprises specific reagents required to practice the inventive method, in particular the diagnostically useful carrier, optionally in addition to one or more solutions required to practice the inventive methods, preferably at least one selected from the group consisting of a sample dilution buffer, washing buffer and buffer comprising a means for detecting any specifically captured antibody, such as a secondary antibody and optionally a means for detecting the latter. Furthermore, it may comprise instructions detailing how to use the kit and the inventive diagnostically useful carrier for contacting the inventive polypeptide with a bodily fluid sample from a subject, preferably a human subject, for example a line blot wherein means for specifically capturing an antibody to the polypeptide according to the present invention is immobilized on the line blot. Furthermore, the kit may comprise a positive control, for example a recombinant antibody known to bind to the polypeptide according to objects of the present invention, and a negative control, for example a protein having no detectable affinity to the polypeptide. Finally, such a kit may comprise a standard solution comprising an antibody for preparing a calibration curve.

In some embodiments, a means for detecting the one or more captured antibodies is required. Various known methods may be used, for example in Zane, H. D. (2001), Immunology—Theoretical & Practical Concepts in Laboratory Medicine, W. B. Saunders Company, in particular in Chapter 14. In one embodiment, a secondary antibody binding to the constant region of one or more captured antibodies, which is the corresponding primary antibody, is used, which secondary antibody may be associated with a label that is straightforward to detect, for example a fluorescent, radioactive or enzymatically active label, the latter of which may catalyze a chemiluminescent reaction or the generation of a molecule detectable using colourimetry or spectroscopy or another analytical method.

Alternatively, a biological functional assay may be used as a means for detecting the one or more captured antibody under the proviso that it is an IgE class antibody, preferably an assay based on basophil activation by IgE antibody. Such assays have been described, for example in Hausmann, O. V., Gentinetta, T., Bridts, C. H., and Ebo, E. G. (2009): The Basophil Activation Test in Immediate-Type Drug Allergy, Immunol. Allergy Clin. N. Am. 29, 555-566.

In one embodiment, the term "diagnosis", as used herein, refers to any kind of procedure aiming to obtain information instrumental in the assessment whether a patient suffers or is likely or more likely than the average or a comparative subject, the latter preferably having similar symptoms, to suffer from a certain disease or disorder in the past, at the time of diagnosis or in the future, to find out how the disease is progressing or is likely to progress in the future or to evaluate the responsiveness of a patient with regard to a certain treatment, for example the administration of suitable drugs such as drugs for the desensitization of allergic patients. In other words, the term "diagnosis" comprises not only diagnosing, but also prognosticating and/or monitoring the course of a disease or disorder or the success of a therapy. It is preferred that IgG, more preferably IgG 4, class autoantibodies detected for the purpose of monitoring the progression of the disease and/or the success of a therapy.

Therefore, the term "diagnosis" does preferably not imply that the diagnostic methods or agents according to the present invention will be definitive and sufficient to finalize the diagnosis on the basis of a single test, let alone parameter, but may refer to a contribution to what is referred to as a "differential diagnosis", i.e. a systematic diagnostic procedure considering the likelihood of a range of possible conditions on the basis of a range of diagnostic parameters. The term "diagnosis" may also refer to a method or agent used to choose the most promising treatment regime for a patient. In other words, the method or agent may relate to selecting a treatment regimen for a subject.

Another object of the present invention is to provide a pharmaceutical composition, preferably a vaccine, comprising the polypeptide according to the invention, which composition is preferably suitable for administration to a subject, preferably a mammalian subject, more preferably to a human. Such a pharmaceutical composition may comprise a pharmaceutically acceptable carrier. The pharmaceutical composition may, for example, be administered orally, parenterally, by inhalation spray, topically, by eyedrops, rectally, nasally, buccally, vaginally or via an implanted reservoir, wherein the term "parenterally", as used herein, comprises subcutaneous, intracutaneous, intravenous, intramuscular, intra-articular, intrasynovial, instrasternal, intrathecal, intralesional and intracranial injection or infusion techniques. The pharmaceutical composition may be provided in suitable dosage forms, for example capsules, tablets and aqueous suspensions and solutions, preferably in sterile form. It may be used in a method of treatment of a disease, preferably an allergy, which method comprises administering an effective amount of the polypeptide to a subject. A hypoallergenic variant of the polypeptide according to the invention may be used. The person skilled in the art is familiar with methods for the generation of hypoallergenic variants of known allergens.

A further object of the present invention is to provide a method for treating, preventing or ameliorating an allergy, preferably a nut allergy, more preferably a macadamia allergy, but administering to a subject the pharmaceutical composition.

All ranges described in this application include all values and subvalues therebetween.

Having generally described this invention, a further understanding can be obtained by reference to certain specific examples which are provided herein for purposes of illustration only and are not intended to be limiting unless otherwise specified.

The present application comprises a number of amino acid sequences, more specifically:

SEQ ID NO:1 (preferred fragment of macadamia vilicin-like protein (Q9SPL3)
SEQ ID NO:2 (fusion protein comprising macadamia vicilin-like protein)
SEQ ID NO:3 (Cor al 1 from hazelnut)
SEQ ID NO:4 (Ses i3 from Sesam)
SEQ ID NO:5 (Ara h1 from peanut)
SEQ ID NO:6 (Pis v3 from pistachio)
SEQ ID NO:7 (Ana o1 from cashew)
SEQ ID NO:8 (Car i2 from pecan)
SEQ ID NO:9 (Jug r2 from walnut)
SEQ ID NO:10 (Mac I vicilin from Macadamia)

EXAMPLES

Example 1

Preparation of Macadamia Nut Extract

Roasted and salted commercially available macadamia nut kernels were ground, followed by defatting 3 times with acetone. The defatted nut debris was dried on a folded filter. The dried material was resuspended in a buffer such as Phosphate buffer saline (PBS, 50 mM sodium phosphate, 150 mM NaCl, pH 7.4) incubated at 4° C. for 3 hours in an incubation shaker, followed by filtration and centrifugation in a benchtop centrifuge for 30 minutes with 4000 rpm at 4° C.

The supernatant was precipitated using 100% ammonium sulfate and the resulting pellet dialysed against PBS. Estimation of protein concentration was performed by Bio-Rad Protein Assay (Bio-Rad Laboratories, Inc., Hercules, USA) as described in the manufacturer's instructions.

Preparative Gel Electrophoresis

The crude macadamia extract was precipitated with cooled acetone and after incubation for 2 hours at −20° C. and centrifugation for 30 minutes at 20000×g at 4° C., the pellet was resuspended in a sample buffer for isoelectric focusing (2.5% sulfobetaine 3-10, 4 M urea, 2 M thiourea, 0.5% (v/v) Carrier Ampholyte pH 3-10, 40 mM DTT and 0.003% bromphenol blue). Overnight the IPG-strip (Ready Strip IPG Strips 7 cm pH 3 to 10 (Bio-Rad), immobilized pH-gradient) was rehydrated with the sample at room temperature.

Subsequently the proteins were focused using a PROTEAN i12 IEF System (Bio-Rad) and separated in the second dimension on the basis of their apparent molecular mass by polyacrylamide gel electrophoresis (4 to 12% Bis-Tris Protein Gels, 1.0 mm×2D well, Thermo Fisher Scientific) using to yield pure protein spots on the gel. For size estimation of the spots in the 2D gel, Spectra Multicolor Broad Range (Thermo Fisher Scientific) was used as described in the manufacturer's instructions.

Figure 1:
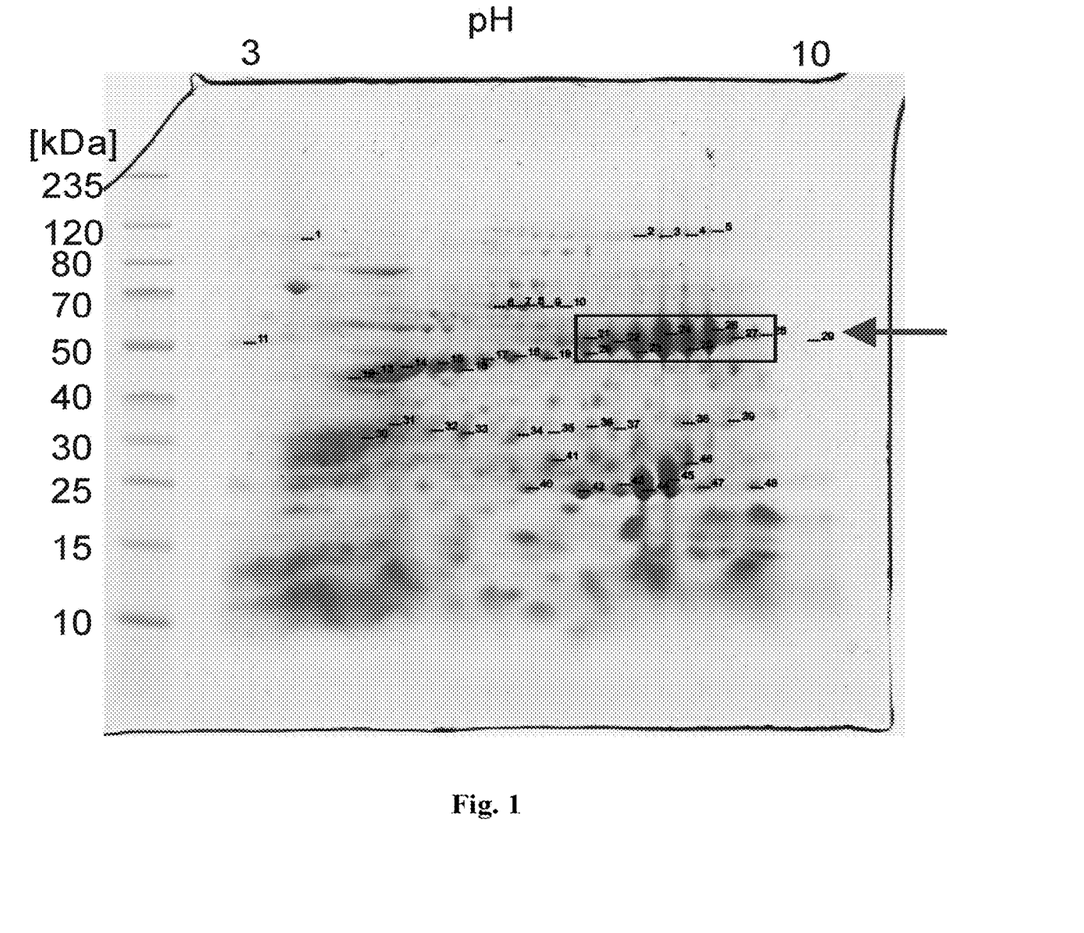
FIG. 1 shows the results of 2D gel electrophoretic separation of a macadamia nut extract. Proteins were separated in the first dimension on a pH 3-10 non-linear IPG strip and subsequently by SDS PAGE under reducing conditions, stained by Coomassie staining and cut out from the gel. Numbers mark the spots subsequently subjected to MALDI-TOF analysis. The arrow marks the band representing the protein subsequently identified as Macadamia vicilin-like protein.

Proteins of the resulting 2D gel were stained by Blue-silver staining (Candiano et al, Electrophoresis. 2004 May; 25(9):1327-33. Blue silver: a very sensitive colloidal Coomassie G-250 staining for proteome analysis). The stained gel is shown in FIG. 1.

Western Blot

The 2D gel of the nut extract was transferred to a nitrocellulose membrane by TE22 Miniblotter (Hoefer Inc., Holliston, Mass., USA) as described in the manufacturer's instructions. The transferred proteins were detected by staining with Ponceau S. The resulting Western blot was incubated for 15 minutes in wash buffer (EUROIMMUN AG, Lübeck, Germany) and subsequently with serum from a macadamia sensitized patient diluted 1:10 in wash buffer for 1 hour.

After washing 3 times for 5 minutes each with wash buffer (Article number ZD1100, as supplied by EUROIMMUN AG for EUROLINE line blots, Lubeck, Germany), the membrane was incubated with anti-IgE-AP conjugate (EUROIMMUN AG, Lübeck, Germany) and again washed 3 times for 5 minutes each with wash buffer. Bound antibodies were detected by incubation with BCIP/NBT substrate (EUROIMMUN AG, Lubeck, Germany) as recommended in the manufacturer's instructions.

Figure 2:
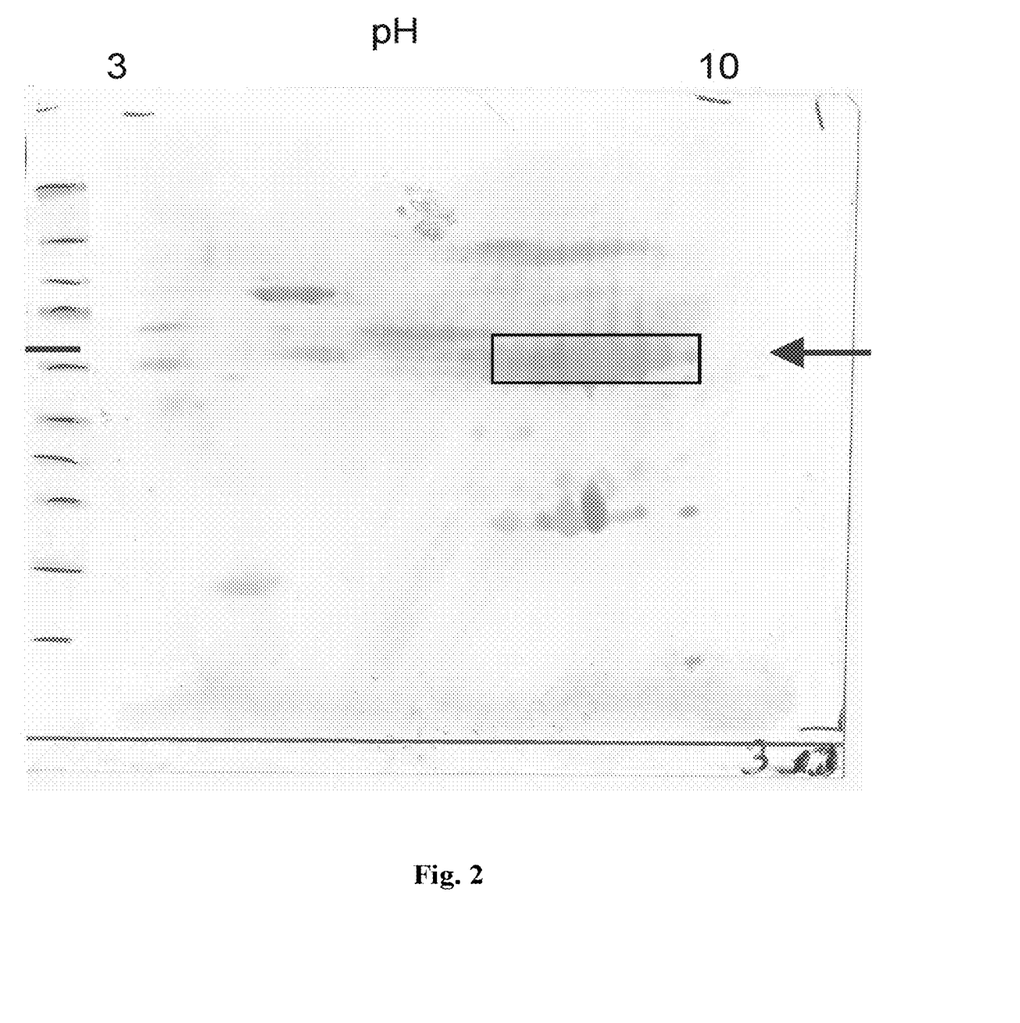
FIG. 2 shows the results of Western blot analysis of a macadamia nut extract and Western blotting of proteins separated by 2D gel electrophoresis. Molecular weight markers are the same as shown in FIG. 1.
Figure 3:
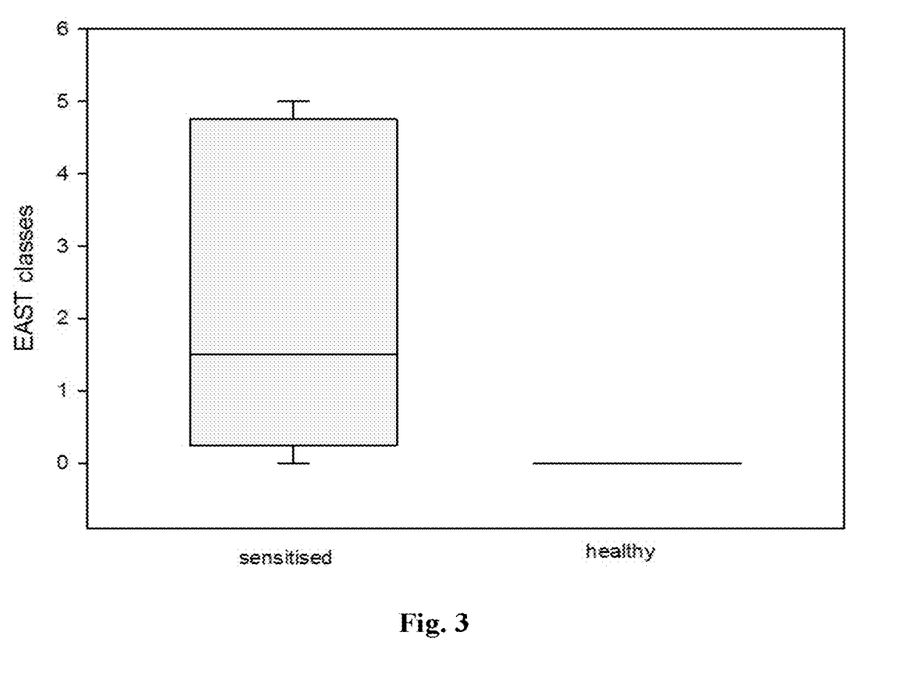
FIG. 3 shows the analysis of human sera from macadamia-sensitized patient (n=20) and healthy blood donors (n=17) using the EUROLINE line assay coated with a vicilin-like protein from macadamia. The evaluation of the bound antibodies from the human sera was carried out based on the EAST reference system.

The obtained blot is shown in FIG. 2. Major proteins of interest include a protein running in the 2D gel electrophoresis at pH 6.3 to 8.7 and 53 to 67 kDa and a protein running in the 2D gel electrophoresis at pH 6.5 to 7.9 and 20 to 25 kDa.

Maldi

The chosen spots of the 2D gel stained with Blue Silver stain were cut out and digested with Trypsin. A peptide mass fingerprint (PMF) and a MSMS were performed with the MALDI-TOF/TOF Autoflex III (Bruker Corporation, Billerica, Mass., USA) as described in the manufacturer's instructions. The NCBI-Database for green plants was screened for convenient sequences, leading to the identification of macadamia vicilin-like protein (Data base accession code is Q9SPL3) as the protein running at pH 6.3 to 8.7 and 53 to 67 kDa.

Cloning, Recombinant Expression and Purification of Macadamia Vicilin-Like Protein The coding region of the macadamia vicilin-like protein, more specifically the coding DNA equivalent to the nucleotide sequence in AF161885 fused via a linker to a His tag as shown in SEQ ID NO:2, was generated by gene synthesis (Eurofins Genomics GmbH), amplified by polymerase chain reaction and subcloned into the recombinant vector using pBAD/TOPO® ThioFusion™ Expression Kits (Invitrogen). The fusion protein was expressed in *E. coli* as described by the manufacturer and isolated by affinity chromatography on nickel matrix (IMAC).

Preparation of a Line Blot (EUROLINE)

The EUROLINE line blot was produced by coating the fusion protein using a precision dispenser (commercially available from Zeta Corporation) onto a nitrocellulose membrane (commercially available from Schleicher & Schüll). After blocking and washing as recommended in the manufacturer's instructions the membrane was cut in 3 mm strips.

Evaluation of Samples Using the EUROLINE Line Assay

The EUROLINE strips were incubated as recommended in the manufacturer's (EUROIMMUN AG, Lübeck, Germany) instructions. In detail the strips were incubated with 1 ml 1/11 (v/v) diluted patient sample (20 macadamia sensitized patients and 17 healthy blood donors) in washing buffer for 16 h at room temperature. After discarding the patient samples the strips were washed 3 times for 5 min with 1 ml washing buffer per strip and subsequently incubated for 1 h with 1 ml anti-human-IgE antibody conjugated with AP. Afterwards the strips were again washed 5 times with washing buffer and then incubated for 10 min with BCIP/NBT substrate.

The evaluation of the results occurred by means of a scanner and EUROLINEScan® program (EUROIMMUN AG, Lübeck, Germany). A semiquantitative analysis can be realized by using an IgE calibration curve of WHO standard (75/502). The IgE concentration is expressed in international units kU/l (kilo IgE units per liter). The results can be interpreted for example using the RAST system (Radioallergo-sorbent test) developed by the company Pharmacia (to date Thermo Scientific) as reference system (Volcheck, Clinical Allergy, Diagnosis and Management, 2009, ISBN 978-1-59745-315-8). The EUROLINEScan® program calculates automatically the intensities of the bands of the EUROLINE into EAST classes (enzyme-allergo-sorbent test), which correlates to the concentration levels of the RAST system. The classification of the EAST classes is shown in Table 1.

TABLE 1

EAST classes

| EAST class | Concentration [kU/l] |
|---|---|
| 0 | <0.35 |
| 1 | 0.35-0.7 |
| 2 | 0.7-3.5 |
| 3 | 3.5-17.5 |
| 4 | 17.5-50 |
| 5 | 50-100 |
| 6 | >100 |

Example 2

Vicilin-like proteins from hazelnut (SEQ ID NO:3), sesame (SEQ ID NO:4), peanut (SEQ ID NO:5), pistachio (SEQ ID NO:6), cashew nut (SEQ ID NO:7), pecan nut (SEQ ID NO:8), walnut (SEQ ID NO:9) and macadamia nut (SEQ ID NO:8) were expressed as His tag fusion proteins according to standard methods and purified as described in example 1.

Line blots were made, contacted with patient samples and evaluated as described in Examples 2 and 3 of EP15001277. Sera from 29 patients allergic to tree nuts and nine healthy blood donors were tested.

The control sera from the healthy blood donors were tested and all found negative (EAST class 0).

FIGS. 4a to 4g show comparative data indicating the IgE concentration expressed in the form of EAST classes in sera from said patients as determined using the line blots. The figures show the correlation between IgE to one tree nut or kernel 7S vicilin-like protein from a tree nut other than Macadamia and the IgE to Mac I Vicilin from Macadamia.

Figure 4:
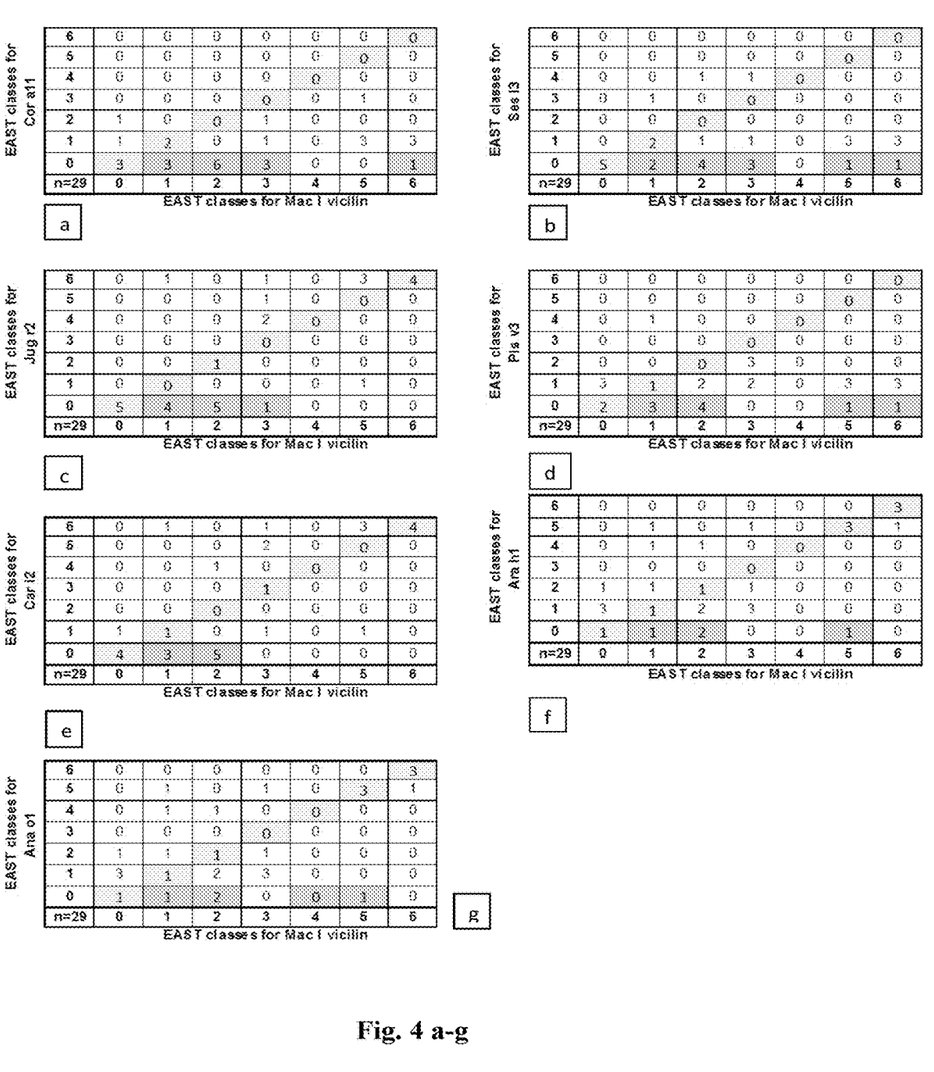
FIGS. 4a to 4g show comparative data indicating the IgE concentration expressed in the form of EAST classes in sera from patients as determined using the line blots.

For example, FIG. 4g shows that one patient showed a EAST class 1, patients an East class 2 and one patient an East class 5 IgE response to Mac I Vicilin, but no response to Ana o1 (cashew nut) as indicated by the fact that they are shown in the line corresponding to 0 EAST class for Ana o1.

These results show that a significant number of allergic patients (dark fields in FIGS. 4a to 4g), in each comparative experiment, react to Mac I Vicilin, but not to the corresponding Vicilin-like protein from the other tree nut, more specifically 13 out of 29 patients (Cor al1 compared to Mac I), 9 out of 29 patients (Ses i3), 10 out of 29 patients (Jug r2), 9 out of 29 patients (Pis v3), 8 out of 29 patients (Car i2), four out of 29 patients (Ara h1) and four out of 29 patients (Ana o1). One of these patients could not be diagnosed by detecting IgE class antibodies to vicilins from other tree nuts rather than Mac I vicilin, since IgE antibodies in his serum reacted to Mac I vicilin only.

There is no EAST class correlation for the Mac I vicilin and the 7S vicilin-like proteins from other nuts and kernels. The reaction of some patients to Mac I vicilin is much stronger than to the respective other tree nut allergen, showing that the respective patient is primarily allergic to Macadamia rather than to another tree nut. For example, FIG. 4a shows that 4 patients have an EAST class of 6 (strong reaction) to Mac I vicilin, but no or only a mild reaction (EAST classes 0 or 1) with regard to Cor al 1. This shows that Mac I Vicilin possesses unique IgE epitopes not shared with any of the other vicilins.

The invention claimed is:

1. A method of detecting an antibody specific to a macadamia protein, the method comprising:

contacting a sample obtained from a subject with at least one macadamia protein selected from the group consisting of the amino acid sequence of SEQ ID NO:1, SEQ ID NO:2, and variants thereof having at least 95% sequence identity to SEQ ID NO: 1 or SEQ ID NO:2 and being at least 150 amino acids in length, wherein the sample is a bodily fluid from a human subject having or suspected of having a nut allergy, detecting whether an antibody to the macadamia protein is present in the sample by detecting a complex between the antibody and the macadamia protein, and optionally, isolating the complex between the antibody and the macadamia protein from the sample.

2. The method of claim 1, wherein the macadamia protein is immobilized on a solid support, and the method further comprising:

washing the immobilized protein in a washing buffer.

3. A method for isolating an antibody binding to a macadamia protein selected from the group consisting of the amino acid sequence of SEQ ID NO:1, SEQ ID NO:2, and variants thereof having at least 95% sequence identity to SEQ ID NO:1 or SEQ ID NO:2 and being at least 150 amino acids in length, the method comprising:
  a) contacting a sample comprising an antibody with the macadamia protein or the variant thereof under conditions compatible with formation of a complex, wherein the complex comprises the antibody and the macadamia protein,
  b) isolating the complex formed in a),
  c) dissociating the complex isolated in b), and
  d) separating the antibody from the macadamia protein.

4. The method according to claim 3, wherein the sample is a bodily fluid selected from the group consisting of whole-blood, serum, cerebrospinal fluid, and saliva.

5. The method of claim 1, wherein the antibody is an IgE antibody.

6. The method of claim 1, further comprising:

detecting an antibody binding to said macadamia protein in said sample with a secondary antibody comprising a label.

7. The method of claim 6, wherein the antibody binding occurs when the subject has a nut allergy.

8. The method of claim 6, wherein the antibody binding occurs when the subject has a macadamia allergy.

9. The method of claim 1, wherein the at least one macadamia protein is a recombinant protein.

\* \* \* \* \*

SEQUENCE LISTING

```
<160> NUMBER OF SEQ ID NOS: 2

<210> SEQ ID NO 1
<211> LENGTH: 177
<212> TYPE: PRT
<213> ORGANISM: Artificial Sequence
<220> FEATURE:
<223> OTHER INFORMATION: Variant of Macadamia vicillin-like protein

<400> SEQUENCE: 1

Gln Cys Met Gln Leu Glu Thr Ser Gly Gln Met Arg Arg Cys Val Ser
1               5                   10                  15

Gln Cys Asp Lys Arg Phe Glu Glu Asp Ile Asp Trp Ser Lys Tyr Asp
            20                  25                  30

Asn Gln Glu Asp Pro Gln Thr Glu Cys Gln Gln Cys Gln Arg Arg Cys
        35                  40                  45

Arg Gln Gln Glu Ser Asp Pro Arg Gln Gln Gln Tyr Cys Gln Arg Arg
    50                  55                  60

Cys Lys Glu Ile Cys Glu Glu Glu Glu Tyr Asn Arg Gln Arg Asp
65                  70                  75                  80

Pro Gln Gln Gln Tyr Glu Gln Cys Gln Lys Arg Cys Gln Arg Arg Glu
                85                  90                  95

Thr Glu Pro Arg His Met Gln Ile Cys Gln Gln Arg Cys Glu Arg Arg
                100                 105                 110
```

```
Tyr Glu Lys Glu Lys Arg Lys Gln Gln Lys Arg Tyr Glu Gln Gln
            115                 120                 125

Arg Glu Asp Glu Glu Lys Tyr Glu Glu Arg Met Lys Glu Gly Asp Asn
130                 135                 140

Lys Arg Asp Pro Gln Gln Arg Glu Tyr Glu Asp Cys Arg Arg His Cys
145                 150                 155                 160

Glu Gln Gln Glu Pro Arg Leu Gln Tyr Gln Cys Gln Arg Arg Cys Gln
                165                 170                 175

Glu

<210> SEQ ID NO 2
<211> LENGTH: 645
<212> TYPE: PRT
<213> ORGANISM: Artificial Sequence
<220> FEATURE:
<223> OTHER INFORMATION: Variant of Macadamia vicillin-like protein with
      His Tag

<400> SEQUENCE: 2

Met Ser His His His His His His Leu Glu Val Leu Phe Gln
1               5                   10                  15

Gly Pro Ser Met Gln Cys Met Gln Leu Glu Thr Ser Gly Gln Met Arg
                20                  25                  30

Arg Cys Val Ser Gln Cys Asp Lys Arg Phe Glu Glu Asp Ile Asp Trp
            35                  40                  45

Ser Lys Tyr Asp Asn Gln Glu Asp Pro Gln Thr Glu Cys Gln Gln Cys
        50                  55                  60

Gln Arg Arg Cys Arg Gln Glu Ser Asp Pro Arg Gln Gln Gln Tyr
65                  70                  75                  80

Cys Gln Arg Arg Cys Lys Glu Ile Cys Glu Glu Glu Glu Tyr Asn
                85                  90                  95

Arg Gln Arg Asp Pro Gln Gln Gln Tyr Glu Gln Cys Gln Lys Arg Cys
                100                 105                 110

Gln Arg Arg Glu Thr Glu Pro Arg His Met Gln Ile Cys Gln Gln Arg
            115                 120                 125

Cys Glu Arg Arg Tyr Glu Lys Glu Lys Arg Lys Gln Gln Lys Arg Tyr
130                 135                 140

Glu Glu Gln Gln Arg Glu Asp Glu Glu Lys Tyr Glu Glu Arg Met Lys
145                 150                 155                 160

Glu Gly Asp Asn Lys Arg Asp Pro Gln Gln Arg Glu Tyr Glu Asp Cys
                165                 170                 175

Arg Arg His Cys Glu Gln Gln Glu Pro Arg Leu Gln Tyr Gln Cys Gln
            180                 185                 190

Arg Arg Cys Gln Glu Gln Arg Gln His Gly Arg Gly Gly Asp Leu
        195                 200                 205

Met Asn Pro Gln Arg Gly Gly Ser Gly Arg Tyr Glu Glu Gly Glu Glu
    210                 215                 220

Lys Gln Ser Asp Asn Pro Tyr Tyr Phe Asp Glu Arg Ser Leu Ser Thr
225                 230                 235                 240

Arg Phe Arg Thr Glu Glu Gly His Ile Ser Val Leu Glu Asn Phe Tyr
                245                 250                 255

Gly Arg Ser Lys Leu Leu Arg Ala Leu Lys Asn Tyr Arg Leu Val Leu
            260                 265                 270

Leu Glu Ala Asn Pro Asn Ala Phe Val Leu Pro Thr His Leu Asp Ala
        275                 280                 285
```

```
Asp Ala Ile Leu Leu Val Ile Gly Gly Arg Gly Ala Leu Lys Met Ile
    290                 295                 300

His Arg Asp Asn Arg Glu Ser Tyr Asn Leu Glu Cys Gly Asp Val Ile
305                 310                 315                 320

Arg Ile Pro Ala Gly Thr Thr Phe Tyr Leu Ile Asn Arg Asp Asn Asn
                325                 330                 335

Glu Arg Leu His Ile Ala Lys Phe Leu Gln Thr Ile Ser Thr Pro Gly
                340                 345                 350

Gln Tyr Lys Glu Phe Phe Pro Ala Gly Gly Gln Asn Pro Glu Pro Tyr
            355                 360                 365

Leu Ser Thr Phe Ser Lys Glu Ile Leu Glu Ala Ala Leu Asn Thr Gln
    370                 375                 380

Thr Glu Arg Leu Arg Gly Val Leu Gly Gln Gln Arg Glu Gly Val Ile
385                 390                 395                 400

Ile Arg Ala Ser Gln Glu Gln Ile Arg Glu Leu Thr Arg Asp Asp Ser
                405                 410                 415

Glu Ser Arg Arg Trp His Ile Arg Arg Gly Gly Glu Ser Ser Arg Gly
                420                 425                 430

Pro Tyr Asn Leu Phe Asn Lys Arg Pro Leu Tyr Ser Asn Lys Tyr Gly
                435                 440                 445

Gln Ala Tyr Glu Val Lys Pro Glu Asp Tyr Arg Gln Leu Gln Asp Met
    450                 455                 460

Asp Val Ser Val Phe Ile Ala Asn Ile Thr Gln Gly Ser Met Met Gly
465                 470                 475                 480

Pro Phe Phe Asn Thr Arg Ser Thr Lys Val Val Val Ala Ser Gly
                485                 490                 495

Glu Ala Asp Val Glu Met Ala Cys Pro His Leu Ser Gly Arg His Gly
                500                 505                 510

Gly Arg Gly Gly Gly Lys Arg His Glu Glu Glu Glu Val His Tyr
        515                 520                 525

Glu Gln Val Arg Ala Arg Leu Ser Lys Arg Glu Ala Ile Val Val Leu
    530                 535                 540

Ala Gly His Pro Val Val Phe Val Ser Ser Gly Asn Glu Asn Leu Leu
545                 550                 555                 560

Leu Phe Ala Phe Gly Ile Asn Ala Gln Asn Asn His Glu Asn Phe Leu
                565                 570                 575

Ala Gly Arg Glu Arg Asn Val Leu Gln Gln Ile Glu Pro Gln Ala Met
                580                 585                 590

Glu Leu Ala Phe Ala Ala Ser Arg Lys Glu Val Glu Glu Leu Phe Asn
    595                 600                 605

Ser Gln Asp Glu Ser Ile Phe Phe Pro Gly Pro Arg Gln His Gln Gln
    610                 615                 620

Gln Ser Pro Arg Ser Thr Lys Gln Gln Gln Pro Leu Val Ser Ile Leu
625                 630                 635                 640

Asp Phe Val Gly Phe
                645
```

UNITED STATES PATENT AND TRADEMARK OFFICE
CERTIFICATE OF CORRECTION

PATENT NO. : 10,842,865 B2
APPLICATION NO. : 15/414380
DATED : November 24, 2020
INVENTOR(S) : Waltraud Suer et al.

Page 1 of 2

It is certified that error appears in the above-identified patent and that said Letters Patent is hereby corrected as shown below:

In the Specification

Column 7, Line 33, currently reads:
"macadamia Vicilin-like protein"

And should read:
--macadamia vicilin-like protein--

Column 13, Line 3, currently reads:
"macadamia vilicin-like protein"

And should read:
--macadamia vicilin-like protein--

Column 16, Line 8, currently reads:
"Mac I Vicilin from Macadamia"

And should read:
--Mac I vicilin from macadamia--

Column 16, Line 11, currently reads:
"Mac I Vicilin"

And should read:
--Mac I vicilin--

Column 16, Line 16, currently reads:
"Mac I Vicilin"

Signed and Sealed this
Twenty-ninth Day of December, 2020

Andrei Iancu
*Director of the United States Patent and Trademark Office*

And should read:
--Mac I vicilin--

Column 16, Line 17, currently reads:
"Vicilin-like protein"

And should read:
--vicilin-like protein--